US012746131B1

(12) United States Patent
Snowden

(10) Patent No.: US 12,746,131 B1
(45) **Date of Patent: *Sep. 29, 2026**

(54) ADJUSTABLE TRIAL SPACER SYSTEM

(71) Applicant: Universal Spine, LLC, Old Hickory, TN (US)

(72) Inventor: Ryan Snowden, Old Hickory, TN (US)

(73) Assignee: Universal Spine, LLC, Old Hickory, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/011,754

(22) Filed: Jan. 7, 2025

Related U.S. Application Data

(63) Continuation of application No. 18/905,831, filed on Oct. 3, 2024, now Pat. No. 12,251,325.

(51) Int. Cl.
*A61F 2/46* (2006.01)
*A61F 2/44* (2006.01)
*A61F 2/30* (2006.01)

(52) U.S. Cl.
CPC .......... *A61F 2/4684* (2013.01); *A61F 2/4455* (2013.01); *A61F 2/4611* (2013.01); *A61F 2002/30324* (2013.01); *A61F 2002/30537* (2013.01); *A61F 2002/4615* (2013.01); *A61F 2002/4629* (2013.01)

(58) Field of Classification Search
CPC .... A61F 2/4684; A61F 2/4455; A61F 2/4611; A61F 2002/30324; A61F 2002/30537; A61F 2002/4615; A61F 2002/4629
USPC ............................... 623/17.11–17.16; 606/99
See application file for complete search history.

(56) References Cited

U.S. PATENT DOCUMENTS

| | | | | |
|---|---|---|---|---|
| 5,702,464 | A * | 12/1997 | Lackey | A61F 2/4684 623/20.32 |
| 6,102,950 | A * | 8/2000 | Vaccaro | A61F 2/4637 606/247 |
| 7,776,095 | B2 * | 8/2010 | Peterman | A61F 2/4684 606/279 |
| 2002/0065560 | A1 * | 5/2002 | Varga | A61F 2/28 623/17.11 |
| 2002/0198532 | A1 * | 12/2002 | Michelson | A61B 17/1671 606/90 |
| 2003/0187506 | A1 * | 10/2003 | Ross | A61F 2/4465 623/17.13 |
| 2004/0019356 | A1 * | 1/2004 | Fraser | A61F 2/4684 623/17.11 |
| 2004/0078079 | A1 * | 4/2004 | Foley | A61F 2/447 623/17.11 |

(Continued)

*Primary Examiner* — Jessica Weiss
(74) *Attorney, Agent, or Firm* — Molly L. Sauter; Trenam Law

(57) ABSTRACT

An adjustable trial spacer system used in spinal surgeries. This system addresses the inefficiencies of traditional trial sizers by introducing a trial base that can be combined with disposable trial caps of varying sizes. The trial base is designed to securely attach to a trial inserter, while the trial caps temporarily enclose the trial base to simulate the final implant. The system's modularity reduces the need for multiple spacer bodies, lowers costs, and improves logistical management in the operating room. Various attachment mechanisms ensure secure fitting during surgical procedures, enhancing precision in determining the appropriate implant size.

16 Claims, 21 Drawing Sheets

(56) References Cited

U.S. PATENT DOCUMENTS

| | | | | | |
|---|---|---|---|---|---|
| 2004/0167537 | A1* | 8/2004 | Errico | A61F 2/442 | 623/17.11 |
| 2004/0176852 | A1* | 9/2004 | Zubok | A61F 2/4611 | 623/17.11 |
| 2004/0215198 | A1* | 10/2004 | Marnay | A61B 17/1735 | 606/86 R |
| 2004/0236342 | A1* | 11/2004 | Ferree | A61B 90/06 | 606/86 R |
| 2005/0038511 | A1* | 2/2005 | Martz | A61B 17/1606 | 623/17.11 |
| 2005/0060034 | A1* | 3/2005 | Berry | A61F 2/44 | 623/17.14 |
| 2005/0071011 | A1* | 3/2005 | Ralph | A61B 17/025 | 606/90 |
| 2005/0261771 | A1* | 11/2005 | Paul | A61F 2/4455 | 623/17.11 |
| 2006/0167551 | A1* | 7/2006 | Stad | A61F 2/4684 | 623/17.13 |
| 2008/0082169 | A1* | 4/2008 | Gittings | A61B 17/025 | 623/23.47 |
| 2008/0215156 | A1* | 9/2008 | Duggal | A61B 17/1666 | 623/18.11 |
| 2010/0292801 | A1* | 11/2010 | Hansell | A61F 2/4684 | 623/17.16 |
| 2010/0298941 | A1* | 11/2010 | Hes | A61F 2/4425 | 623/17.16 |
| 2010/0305711 | A1* | 12/2010 | McKinnon | A61B 17/157 | 606/82 |
| 2013/0006370 | A1* | 1/2013 | Wogoman | A61F 2/4684 | 623/20.16 |
| 2015/0073555 | A1* | 3/2015 | To | A61F 2/442 | 623/17.16 |

* cited by examiner

ADJUSTABLE TRIAL SPACER SYSTEM

PRIORITY INFORMATION

This nonprovisional application is a continuation of and claims priority to nonprovisional application Ser. No. 18/905,831, entitled "Adjustable Trial Spacer System," filed Oct. 3, 2024 by the same inventor.

BACKGROUND OF THE INVENTION

Field of the Invention

This invention relates, generally, to trial spacers for surgical procedures.

Brief Description of the Prior Art

In spinal surgery, the precise restoration of the intervertebral disc space is critical for ensuring proper alignment, stability, and overall success of the procedure. To achieve this, surgeons typically use trial sizers, also known as "trial spacers," during the surgical process. These trial sizers are temporary devices inserted into the disc space to simulate the final implant, allowing the surgeon to determine the correct size, and fit before implanting the permanent spacer or cage.

Traditional trial sizer kits consist of multiple complete trial sizers of varying sizes to accommodate the different anatomical needs of patients. These trial sizers usually include spacer bodies permanently secured to a handle and are usually made from durable, reusable materials such as stainless steel or titanium. While effective, these kits come with several disadvantages. The manufacturing and sterilization processes involved make these spacer bodies expensive, and the need to maintain a wide range of sizes increases the overall cost and complexity of the kit. Moreover, the handling and storage of multiple spacer bodies add to the logistical burden for healthcare providers.

Given these challenges, there is a need for a more cost-effective and efficient solution that allows surgeons to perform accurate trials. The inventive approach disclosed herein is to introduce a base trial spacer that can be used in conjunction with a series of disposable caps. These caps, which come in various sizes, can be easily secured to the base trial spacer, creating the necessary height and profile for different patient anatomies. This system not only reduces the number of spacer bodies required but also lowers the overall cost by utilizing cheaper, disposable components for size variation. The proposed invention aims to meet this need by providing a novel trial spacer system that enhances surgical efficiency while maintaining the precision required for successful spinal procedures.

However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a more cost-effective and efficient trial spacer system is now met by a new, useful, and nonobvious invention.

The novel structure includes an adjustable trial spacer system. The system includes a trial base that has a predetermined thickness and an attachment feature configured to engage a trial inserter. The system may further include a trial inserter. Moreover, the attachment feature in the trial base can be in the form of a threaded aperture configured to threadedly engage the trial inserter.

The present invention further includes a plurality of trial caps. Each trial cap has a predetermined thickness that is greater than the predetermined thickness of the trial base and distinct from other trial caps. In addition, each trial cap has a first section and a second section that are configured to temporarily house at least a portion of the trial base.

In some embodiments the first section and the second section of each trial cap further include a recess configured to receive a portion of the trial base. Each trial cap may also include an aperture that aligns with the attachment feature in the trial base when the trial base resides within the trial cap.

Each trial cap further includes one or more interlocking components to securely attach the first section to the second section. In some embodiments, the one or more interlocking components further include an extension projecting inwardly from the first section and a receipt extending inwardly from the second sections. The receipt is configured to engage the extension when the first section and the second section are attached, Moreover, the trial base includes an aperture configured to enable passage of the extension therethrough.

In some embodiments, the trial base has a tapered profile. The trial cap may also or alternatively have a tapered profile.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

Figure 1:
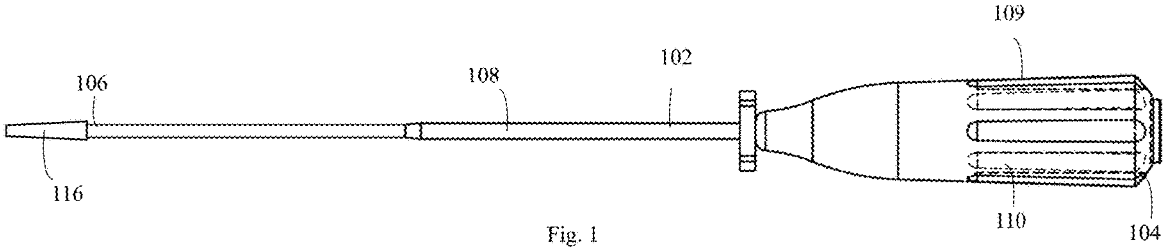
FIG. 1 is a side view of an embodiment of the trial inserter and the trial base attached thereto.

In the following detailed description of the present invention, reference is made to the accompanying drawings, which form a part thereof, and within which are shown by way of illustration specific embodiments by which the invention may be practiced. Numerous specific details are set forth to provide a thorough description of the embodiments of the present invention. It will be apparent to one of ordinary skill in the art that some embodiments may be practiced without some of these specific details. It is to be understood that other embodiments may be utilized, and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

All numerical designations, such as measurements, efficacies, physical characteristics, forces, and other designations, including ranges, are approximations which are varied up or down by increments of 1.0 or 0.1, as appropriate. It is to be understood, even if it is not always explicitly stated that all numerical designations are preceded by the term "approximately." As used herein, "approximately" refers to being within an acceptable error range for the particular value as determined by one of ordinary skill in the art, which will depend in part on how the value is measured or determined. When an acceptable range is not dictated by the one of ordinary skill in the art, "approximately" refers to ±15% of the numerical when used in connection with particular values; it should be understood that a numerical including an associated range with a lower boundary of greater than zero must be a non-zero numerical, and the term "approximately" should be understood to include only non-zero values in such scenarios.

The phrases "in some embodiments," "according to some embodiments," "in the embodiments shown," "in other embodiments," and the like generally mean the particular feature, structure, or characteristic following the phrase is included in at least one implementation. In addition, such phrases do not necessarily refer to the same embodiments or different embodiments.

The present invention includes a series of trial caps of differing sizes, which are configured to securely and temporarily attach to or at least partially house a trial base. The trial base is attachable to a trial inserter, thereby allowing a surgeon to quickly and easily adjust the size of the insertable trial to determine the appropriate size of a required implant. As used herein, the term "insertable trial" refers to the either a trial base intended to be inserted into a patient or a combination of the trial base and at least one of the trial caps when the trial cap at least partially encloses the trial base and the combination is to be inserted into the patient. It should be noted that, for the sake of brevity, exemplary trial caps are depicted in the figures instead of displaying all of the plurality of trial caps for each embodiment.

Referring now to FIGS. 1-3, 15-16, and 36-37, embodiments of the present invention include trial inserter 102. Trial inserter 102 includes proximal end 104 and distal end 106. Shaft 108 extends between proximal end 104 and distal end 106. Proximal end 104 includes handle section 109, which is sufficiently sized to be grasped by a user and may include grip enhancing features 110. Grip enhancing features include but are not limited to grooves, knurling, ribbing, or cross-hatching, to prevent slippage.

Shaft 108 may be comprised of a single shaft or may be a multi-part construction. In some embodiments, shaft 108 may be adjustable in length, using for example a telescoping arrangement of shafts. Shaft 108 may also be temporarily attachable to handle section 109 thereby allowing a user to switch out one shaft for another having a different overall length.

Figure 2:
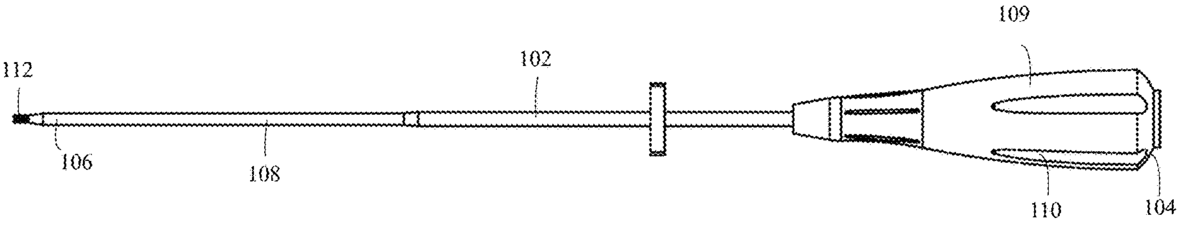
FIG. 2 is a side view of an embodiment of the trial inserter with the trial base removed.

As best depicted in FIG. 2, distal end 106 of trial inserter 102 includes thread 112. Thread 112 is configured to engage a corresponding threaded receipt 114 in trail base 116. However, it is contemplated that some embodiments may use alternative approaches and devices for attaching trial base 116 to trial inserter 102, including but not limited to a bayonet locking mechanism, in which shaft 108 is inserted into trial base 116 and twisted to lock in place using interlocking grooves; a snap-fit connection, where flexible tabs on shaft 108 engage with slots in trial base 116; a press-fit attachment, where shaft 108 is forced into a slightly undersized hole to create a tight fit; a pin-and-hole connection, where a removable pin is inserted through aligned holes in both shaft 108 and trial base 116; and magnetic coupling, where embedded magnets in shaft 108 and trial base 116 hold them together.

In some embodiments, trial inserter 102, or at least the distal portion 106 and shaft 108 are comprised of a biocompatible material. Trial inserter 102 may also be comprised of a material sufficient to withstand surgical sanitization methods, such as sanitization through an autoclave. Non-limiting examples of biocompatible materials include titanium and titanium alloys, such as Ti-6Al-4V; stainless steel, particularly 316L surgical grade; PEEK (polyetheretherketone); cobalt-chromium alloys; medical-grade plastics, such as UHMWPE (Ultra-High Molecular Weight Polyethylene); ceramics; such as alumina or zirconia; and carbon fiber-reinforced polymers.

Trial base 116 is configured to attach to trial inserter 102 and function as the smallest trial spacer for insertion between a patient's vertebrae. Thus, like trial inserter 102, trial base 116 is also comprised of biocompatible material and/or a material configured to withstand surgical sanitization methods. Non-limiting examples of such materials include titanium and titanium alloys, stainless steel, PEEK, cobalt-chromium alloys, medical-grade plastics, ceramics, and carbon fiber-reinforced polymers.

As best depicted in FIGS. 4-5, 17-18, and 38-41, trial base 116 includes proximal end 118 and distal end 120 with body section 122 residing therebetween. When viewed from the top or bottom (see, e.g. FIG. 5), body section 122 may have a generally square shape with a length 'L' (distance between the proximal and distal ends) of approximately 26 mm and a width 'W' of approximately 30 mm. As depicted in FIG. 15-18, body section 122 may have a generally rectangular shape with a length 'L' of approximately 26 mm and a width 'W' of approximately 17 mm. In other embodiments, body section 122 may have a generally oval shape as shown in FIGS. 38-44, with a major axis of approximately 33 mm and a minor axis of approximately 28 mm. It is also contemplated that other shapes may be used. It should be noted that alternative sizes are also contemplated.

Trial base 116 may also include a wedge-like or tapered shape. In some embodiments, trail base 116 narrows in thickness moving from proximal end 118 to distal end 120, i.e., trial base 116 has a converging taper moving in a distal direction. In some embodiments, the tapered equates to the top and bottom surfaces each having a slope of approximately 3 degrees, which totals approximately 6 degrees between the two surfaces. It should be noted that non-tapered shapes and alternative degrees of taper are also contemplated.

Figure 5:
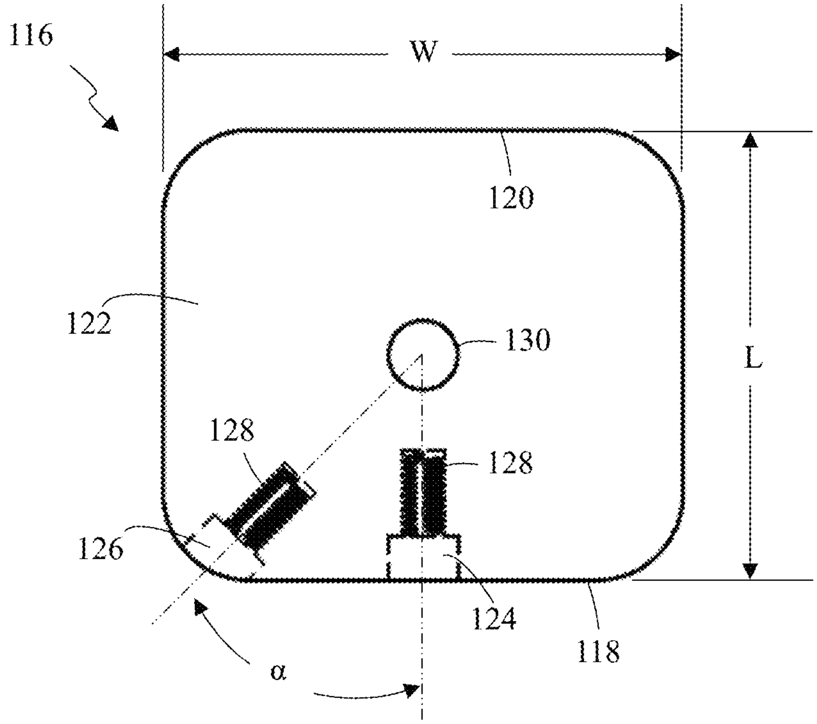
FIG. 5 is a top view of an embodiment of a trial base.
Figure 6:
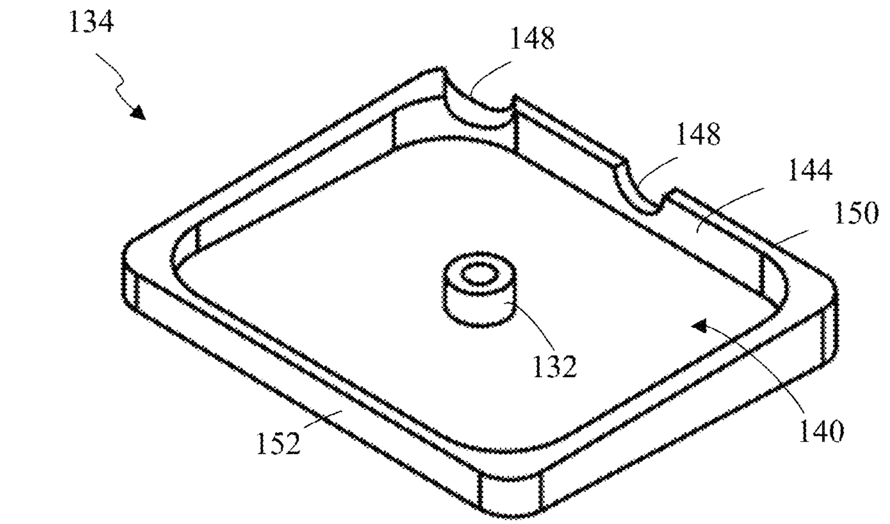
FIG. 6 is a perspective view of an embodiment of a first section of a trial cap.
Figure 7:
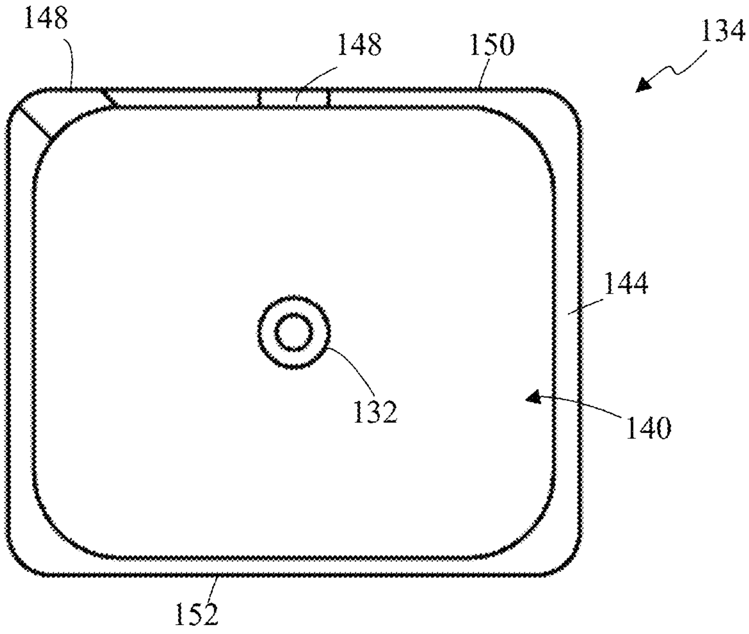
FIG. 7 is a bottom view of an embodiment of a first section of a trial cap.
Figure 8:
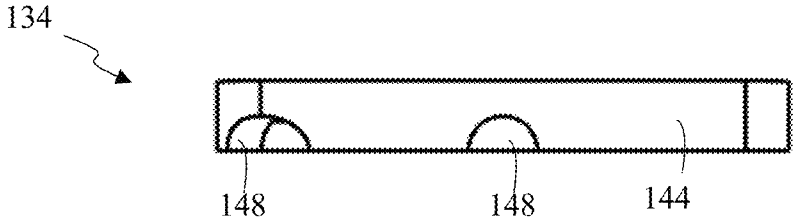
FIG. 8 is an end view of an embodiment of a first section of a trial cap.
Figure 17:
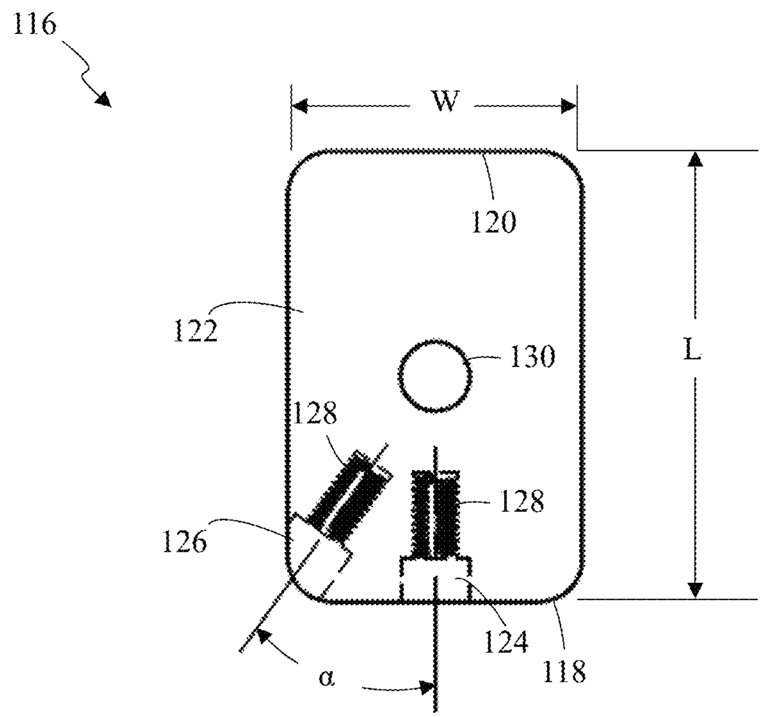
FIG. 17 is a top view of an embodiment of a trial base.
Figure 18:
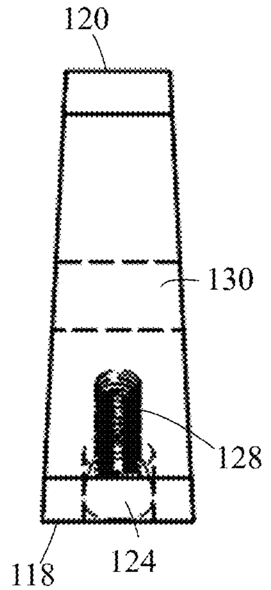
FIG. 18 is a side profile view of an embodiment of a trial base.
Figure 19:
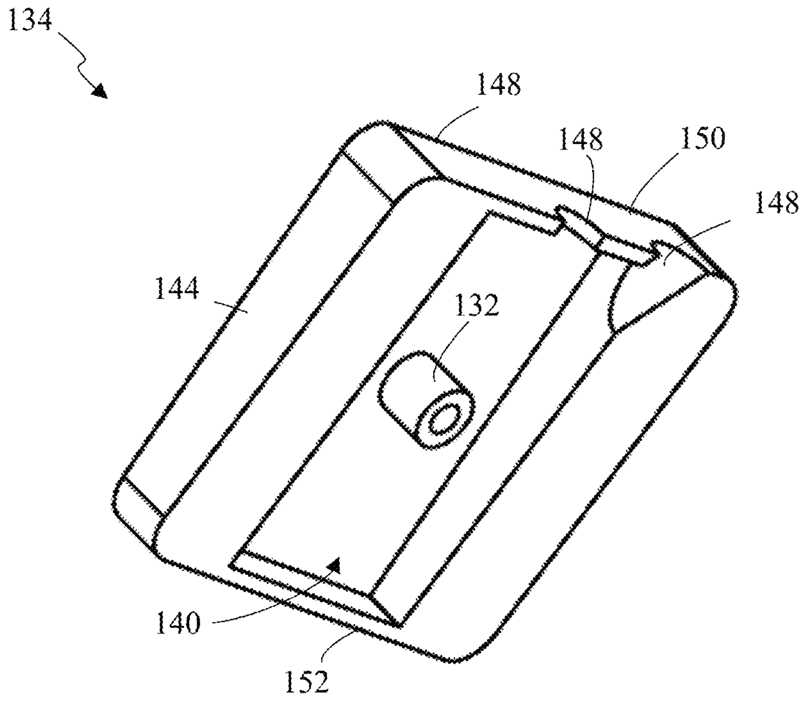
FIG. 19 is a perspective view of an embodiment of a first section of a trial cap.
Figure 20:
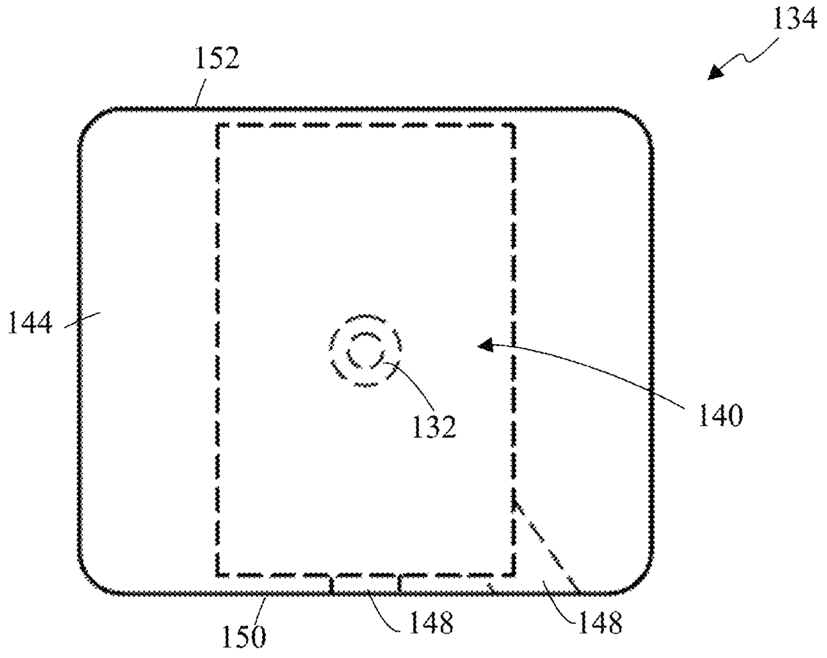
FIG. 20 is a bottom view of an embodiment of a first section of a trial cap.
Figure 21:
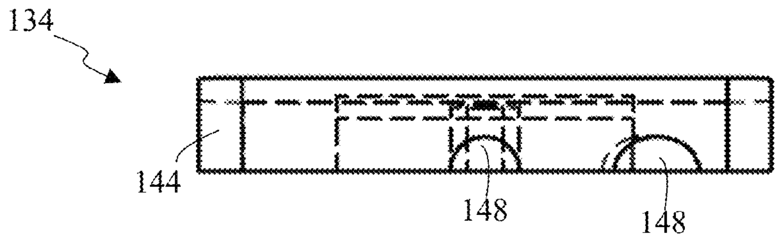
FIG. 21 is an end view of an embodiment of a first section of a trial cap.
Figure 22:
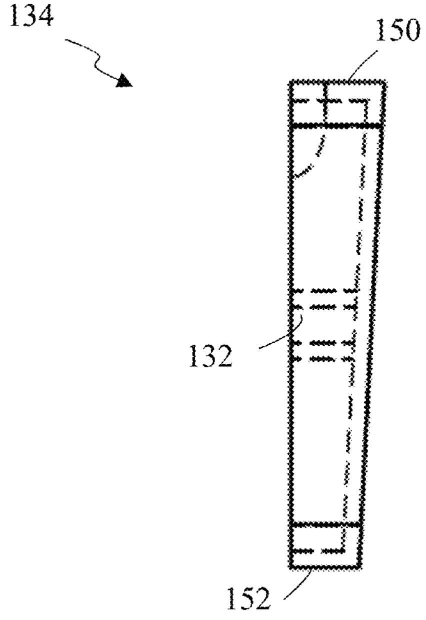
FIG. 22 is a side profile view of an embodiment of a first section of a trial cap.
Figure 23:
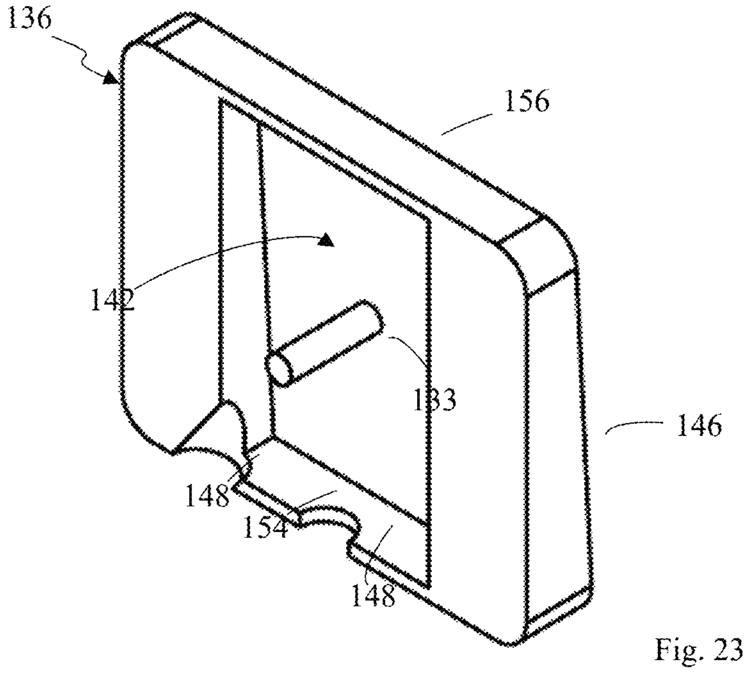
FIG. 23 is a perspective view of an embodiment of a second section of a trial cap.
Figure 24:
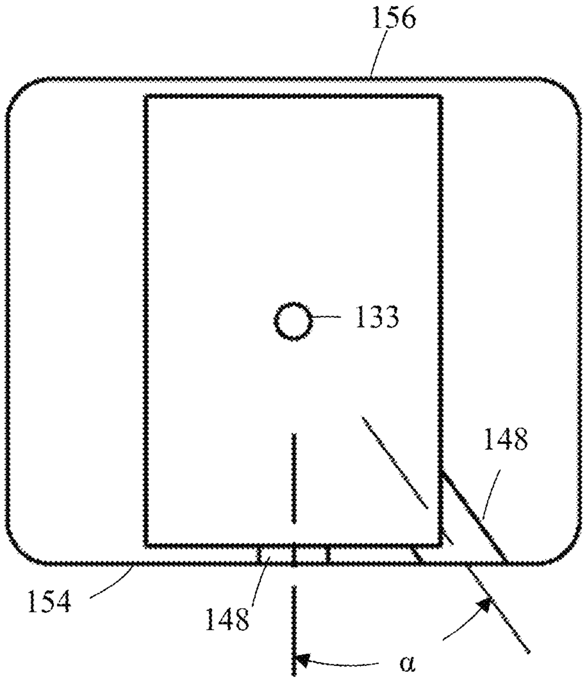
FIG. 24 is a top view of an embodiment of a second section of a trial cap.
Figure 25:
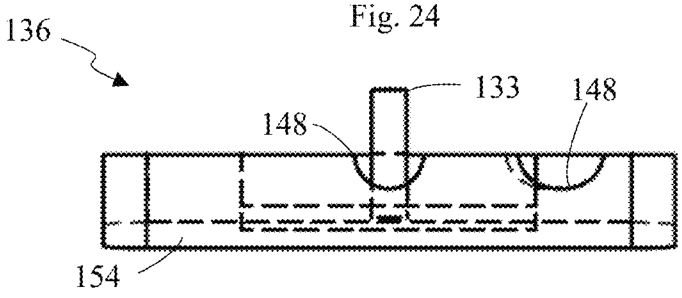
FIG. 25 is an end view of an embodiment of a second section of a trial cap.
Figure 39:
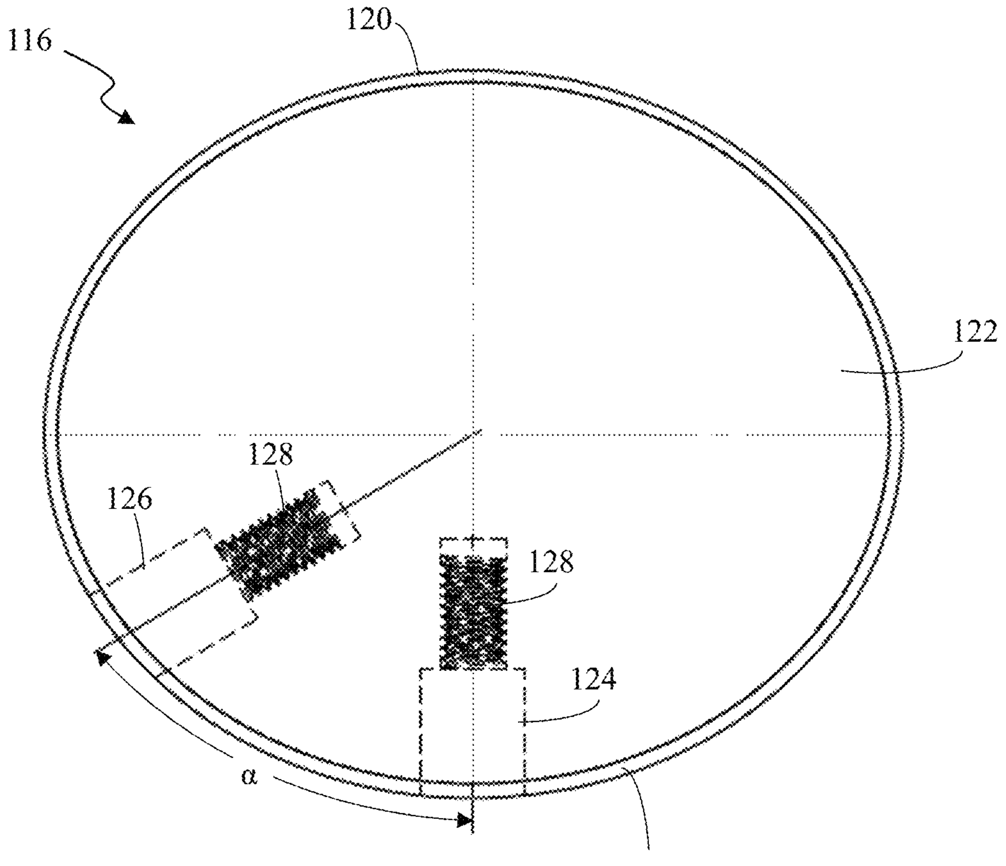
FIG. 39 is a top view of an embodiment of a trial base.
Figure 40:
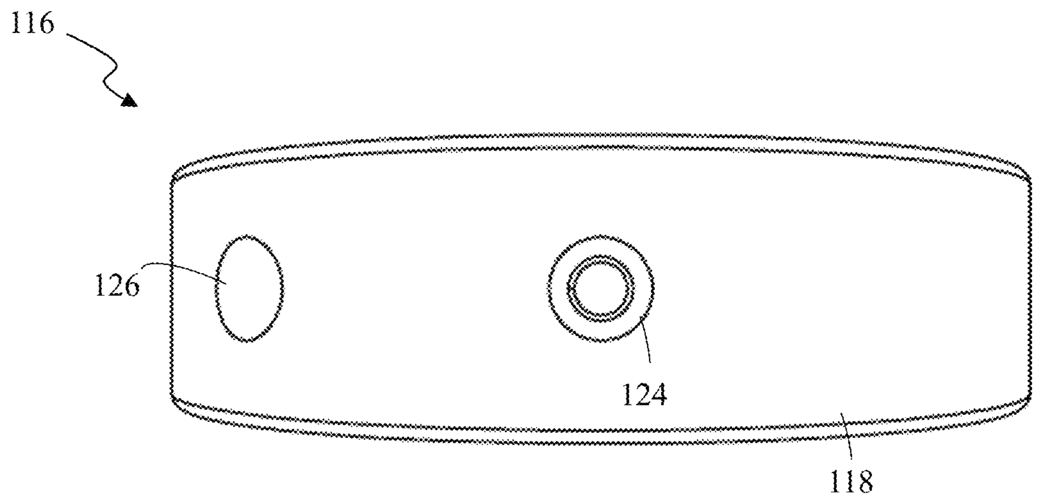
FIG. 40 is an end view of an embodiment of a trial base.
Figure 41:
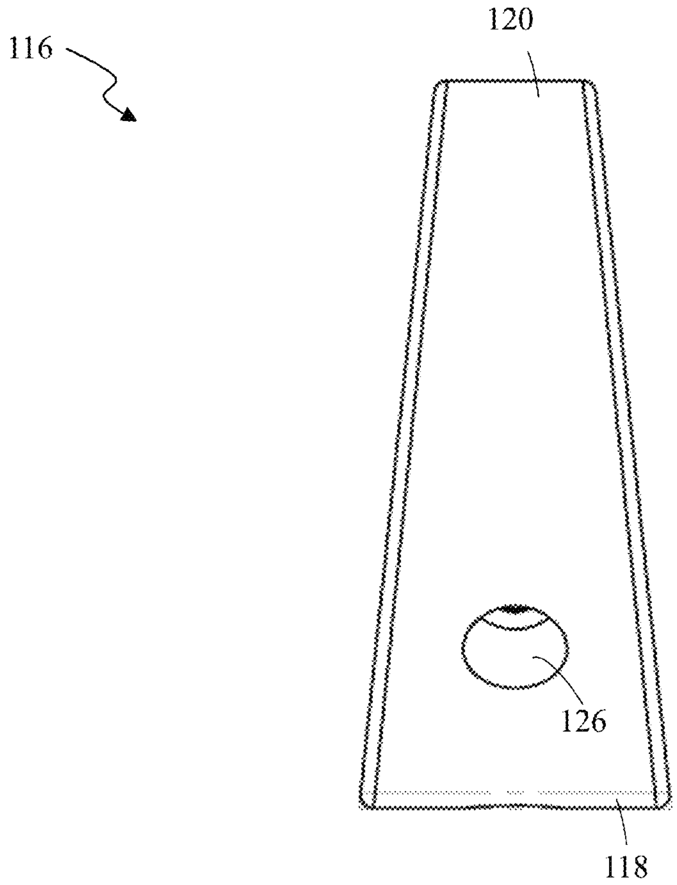
FIG. 41 is a side profile view of an embodiment of a trial base.

Trial base 116 further includes one or more receipts for coupling trial base 116 to trial insert 102. A first receipt 124 is aligned with the central longitudinal axis of trial base 116 and is generally located in proximal end 118 at the halfway point between the top and bottom surfaces of trial base 116. Some embodiments also or alternatively include a second receipt 126 that is offset from the central longitudinal axis of trial base 116. Second receipt 126 may also be oriented at angle 'a' relative to the central longitudinal axis as best depicted in FIGS. 5, 17, and 39. While the provided embodiments depict angle 'a' as approximately 45 degree, 35 degrees, and 60 degrees, respectively, it is contemplated that angle 'a' have alternative values to align shaft 108 with a center point of body section 122 and/or ensure that second receipt 126 remains proximate proximal end 118.

One or both of first receipt 124 and second receipt 126 may include a threaded section 128 for operably engaging threaded section 112 of trial inserter 102. However, alternative engagement methods and devices may be employed to secured distal end 106 of trial inserter 102 to trial base 116, including but not limited to a bayonet lock, quick release pin mechanism, snap-fit connection, magnetic attachment, and press-fit connection.

In some embodiments, as depicted in FIGS. 4-5 and 17-18, trial base 116 further includes aperture 130 disposed through body section 122. Aperture 130 is sized to receive one or more extensions 132 and 133 protruding from sections 134 and 136 of trial caps 138 to retain trial caps 138 to trial base 116. Similarly, aperture 130 includes a complimentary shape to receive and retain extensions 132 and/or 134 of trial caps 138.

Aperture 130 may be located at the center point of body section 122. Such a location reduces the chances of unwanted moment forces applied to trial caps 138 when trial inserter 104 and trial base 116 encounter resistance forces.

In some embodiments, aperture 130 may be in an alternative form rather than a through hole. For example, aperture 130 may be in the form of indentations, grooves, or other surface features configured to interact with corresponding extensions from trial caps 138 to aid in the retention of trial caps 138 to trial base 116.

Referring now to FIGS. 6-14 and 19-27, the present invention may include one or more trial caps 138. In some embodiments, the present invention includes a plurality of trial caps 138 each having a different thickness to allow a surgeon to trial spacers of differing thicknesses/heights to identify the proper sizing of an implant. For the sake of brevity, the figures depict only a single trial cap 138 instead of the plurality.

Figure 3:
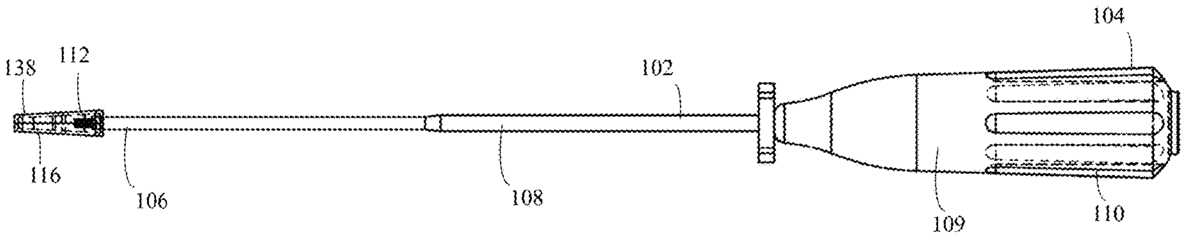
FIG. 3 is a side view of an embodiment of the trial inserter and the trial base with a trial cap attached to the trial base.
Figure 4:
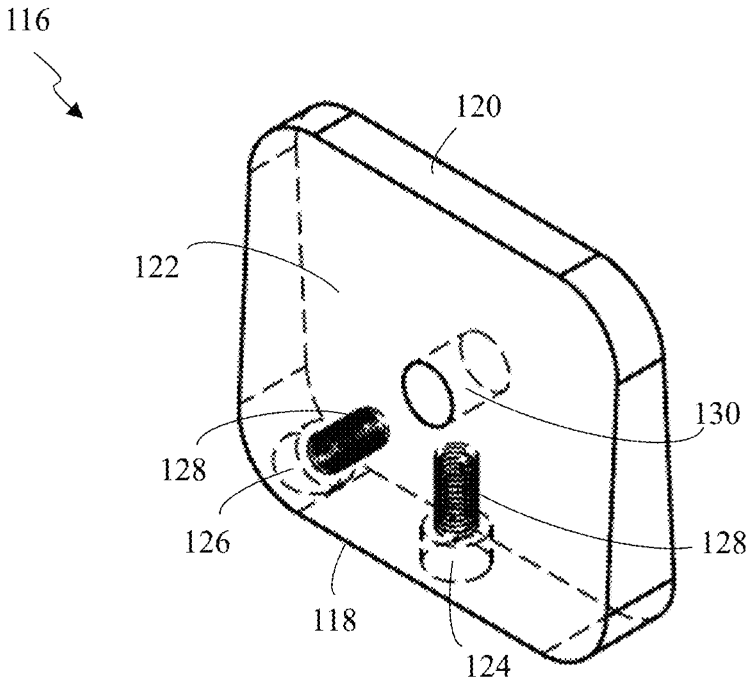
FIG. 4 is a perspective view of an embodiment of a trial base.
Figure 14:
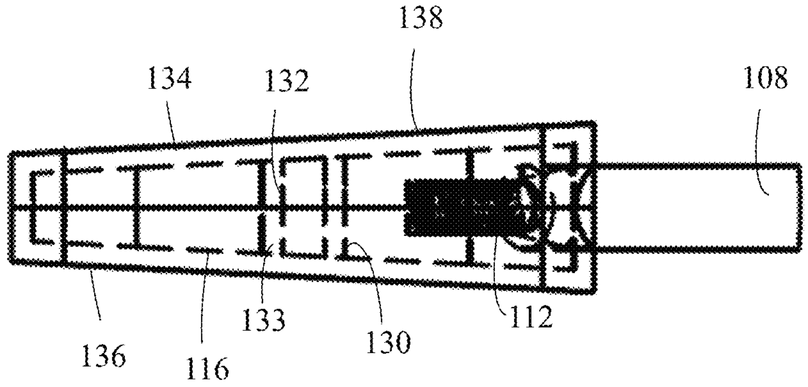
FIG. 14 is a close-up view of a trial cap secured to a trial base showing the internal components in dashed lines.
Figure 15:
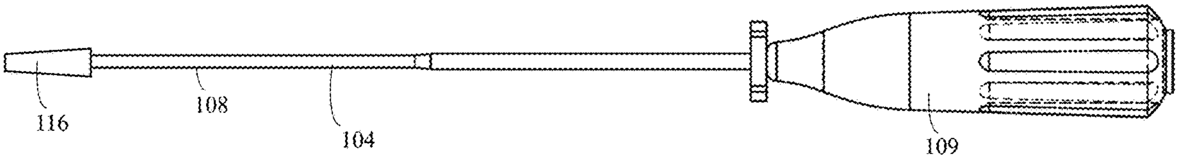
FIG. 15 is a side view of an embodiment of the trial inserter and the trial base attached thereto.
Figure 16:
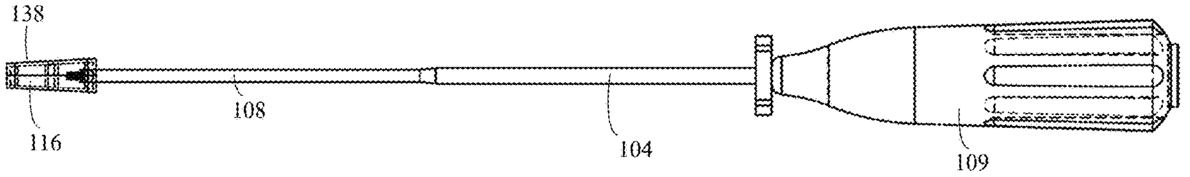
FIG. 16 is a side view of an embodiment of the trial inserter and the trial base with a trial cap attached to the trial base.
Figure 27:
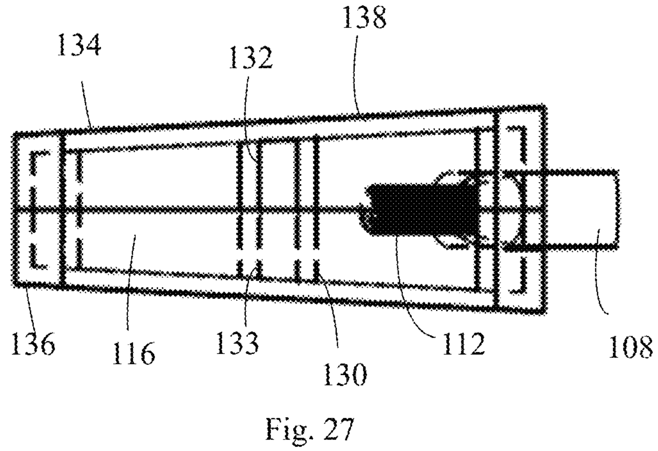
FIG. 27 is a close-up view of a trial cap secured to a trial base showing the internal components in dashed lines.

Trial caps 138 have first section 134 and second section 136, which are configured to at least partially house trial base 116 as depicted in FIGS. 3, 14, and 27. In some embodiments, first section 134 and second section 136 completely enclose trial base 116. To do so, first section 134 and second section 136 each include receiving area 140 and 142 recessed into first section 134 and second section 136, respectively. Each receiving area 140 and 142 has a size and shape sufficient to receive approximately half, or at least a portion of, trial base 116.

Receiving areas 140 and 142 are established at least in part by sidewalls 144 and 146 extending inwardly from first section 134 and second section 136, respectively. Sidewalls 144 and 146 are sized and configured to prevent trial base 116 from unexpectedly exiting trial caps 138. In addition, sidewalls 144 and 146 include apertures 148 that align with receipts 124 and 126 in trial base 116 when trail base 116 is disposed within trial caps 138.

First section 134 and second section 136 are also designed and configured to mate with each other through one or more interlocking components. For example, the embodiments in FIGS. 9-14 and 19-27 include extension 132 protruding inwardly from first section 134 and extension 133 protruding inwardly from second section 136. Extensions 132 and 133 are not only configured to aid in the retention of trial caps 138 to trial base 116, but are also configured to temporarily engage each other to maintain the connection between first section 134 and second section 136.

In some embodiments, extension 132 is configured to receive extension 133, or vice versa, to establish an interference fit and thereby temporarily couple first section 134 and second section 136 to one another. However, alternative methods and devices can be used to attach extensions 132 and 133 to each other. In addition, alternative methods and devices can be used to attach first section 134 and second section 136 to each other.

Figure 9:
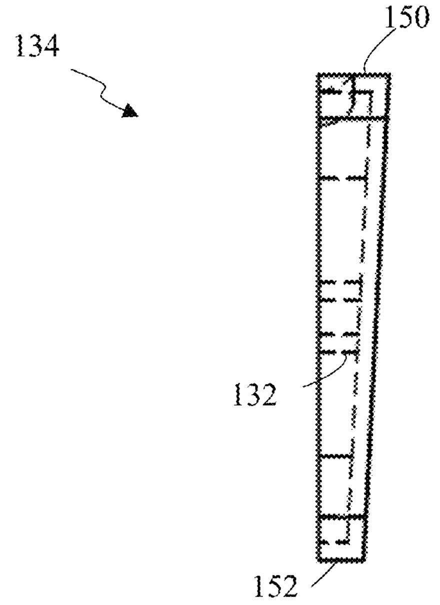
FIG. 9 is a side profile view of an embodiment of a first section of a trial cap.
Figure 10:
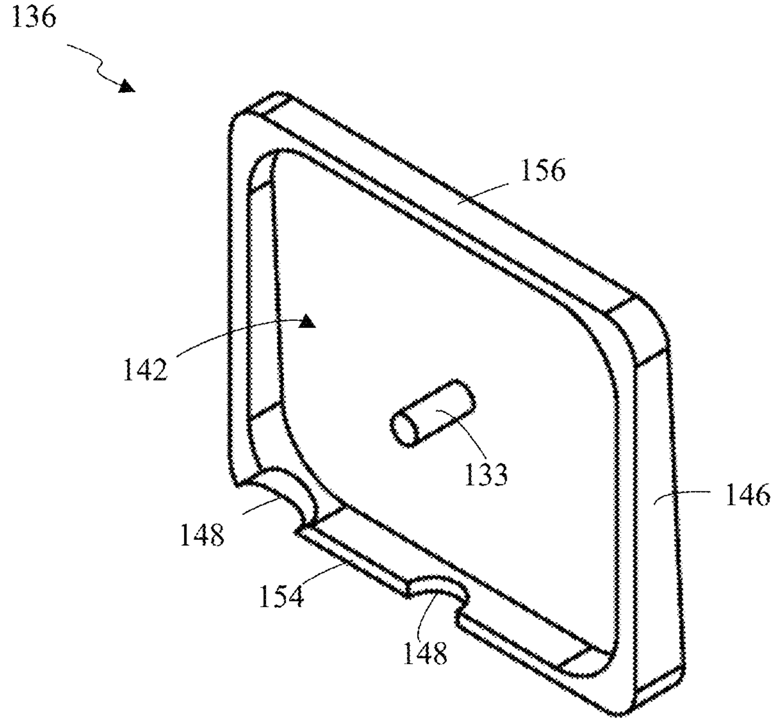
FIG. 10 is a perspective view of an embodiment of a second section of a trial cap.
Figure 11:
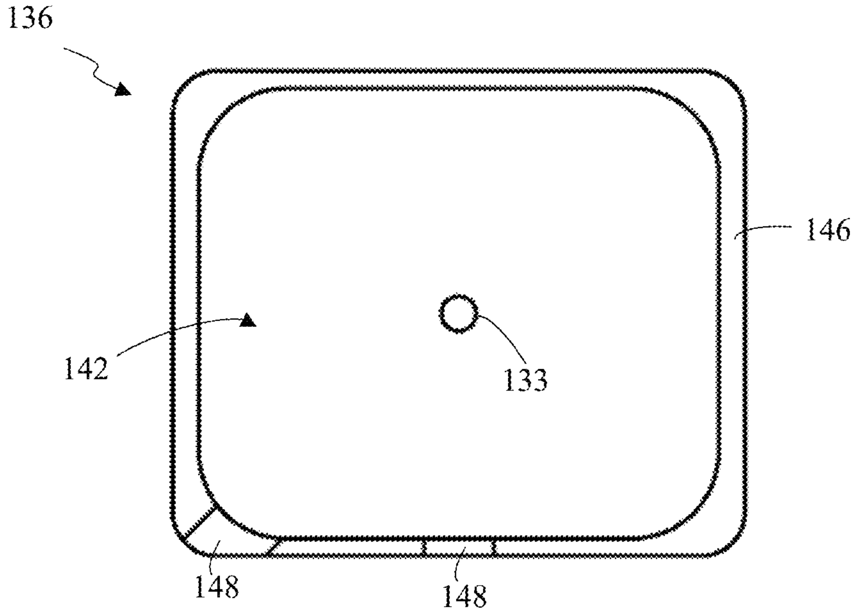
FIG. 11 is a top view of an embodiment of a second section of a trial cap.
Figure 12:
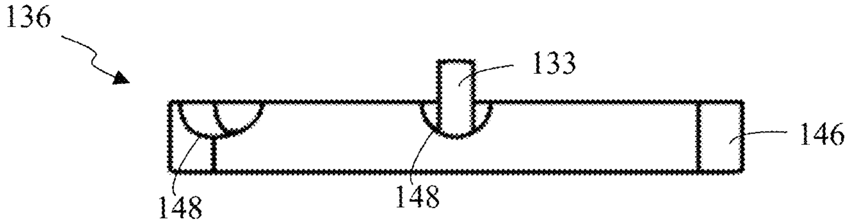
FIG. 12 is an end view of an embodiment of a second section of a trial cap.
Figure 13:
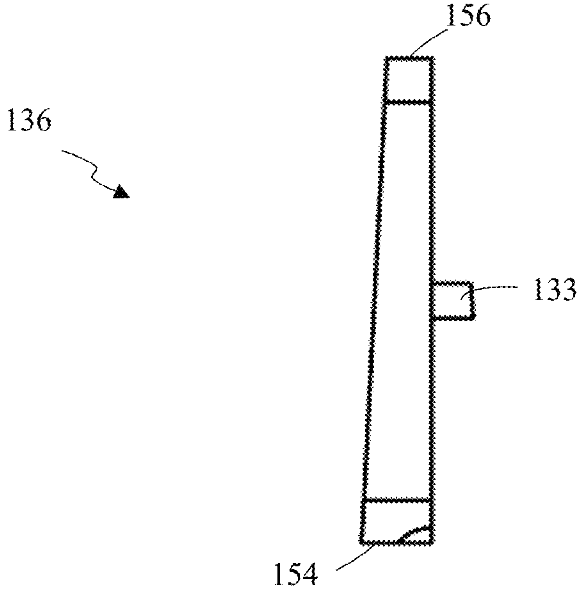
FIG. 13 is a side profile view of an embodiment of a second section of a trial cap.
Figure 26:
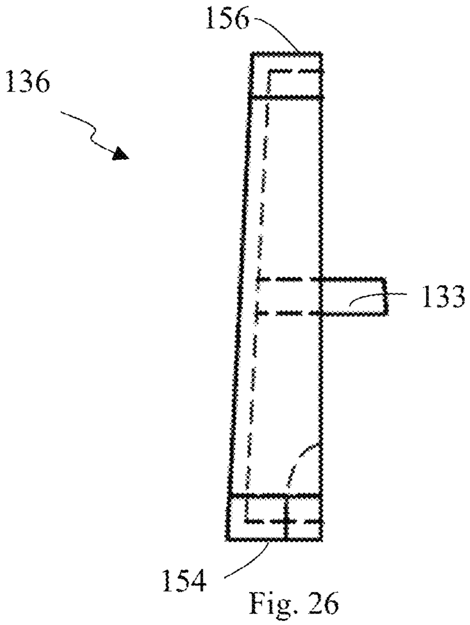
FIG. 26 is a side profile view of an embodiment of a second section of a trial cap.

While trial caps 138 increase the overall thickness of the insertable trial (i.e., the combination of trial base 116 and trial caps 138), they also maintain the same distally directed taper as trial base 116. To do so, first section 134 is tapered moving in a distal direction from proximal end 150 to distal end 152 and second section 136 is tapered moving in a distal direction from proximal end 154 to distal end 156 as best depicted in FIGS. 9, 13, and 26. However, some embodiments of trial caps 138 may lack a taper or be tapered in a different direction.

Like the other components, trial caps 138 may be comprised of a biocompatible material. Again, non-limiting examples of biocompatible materials include titanium and titanium; stainless steel; PEEK; cobalt-chromium alloys; medical-grade plastics; ceramics; and carbon fiber-reinforced polymers. Trial caps 138 may also be comprised of a material sufficient to withstand surgical sanitization methods, such as sanitization through an autoclave. However, some embodiments may be comprised of material not intended for reuse or sanitization.

Figure 28:
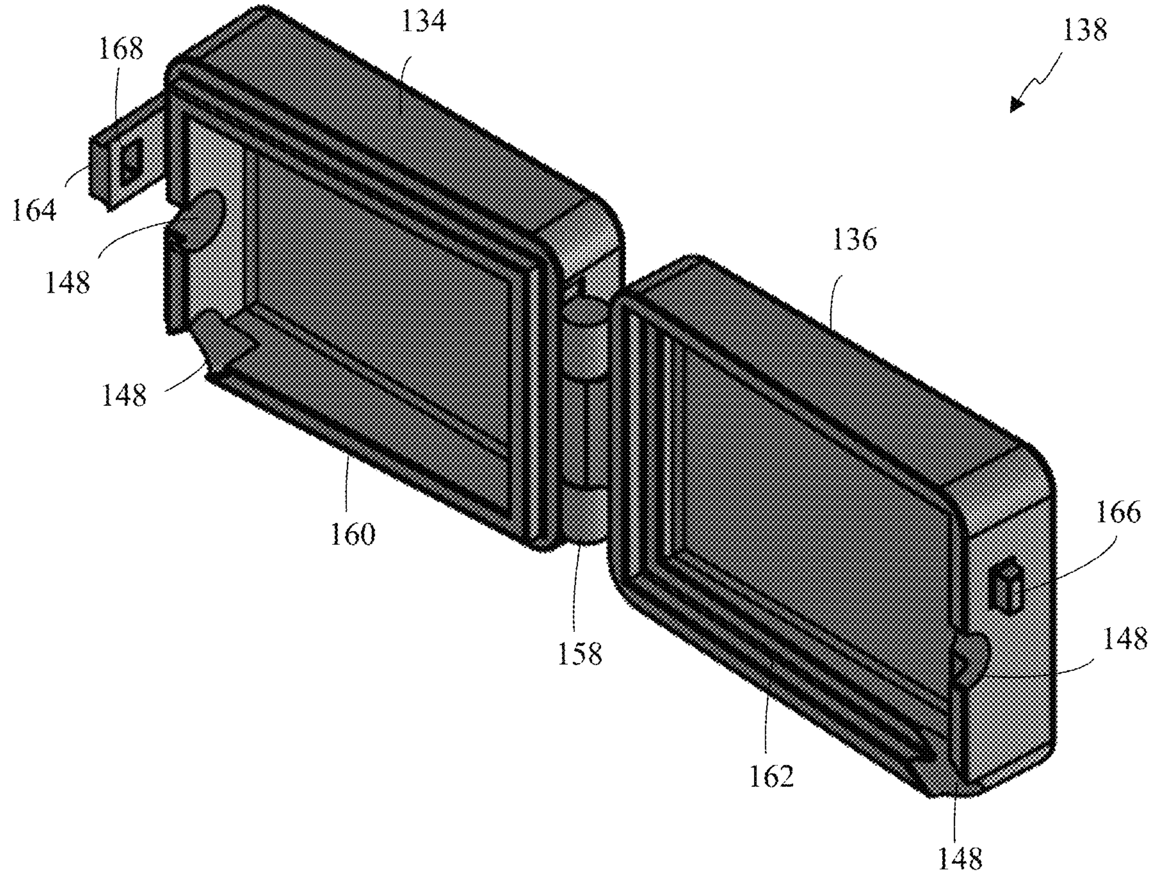
FIG. 28 is a perspective view of an embodiment of a trial cap.
Figure 29:
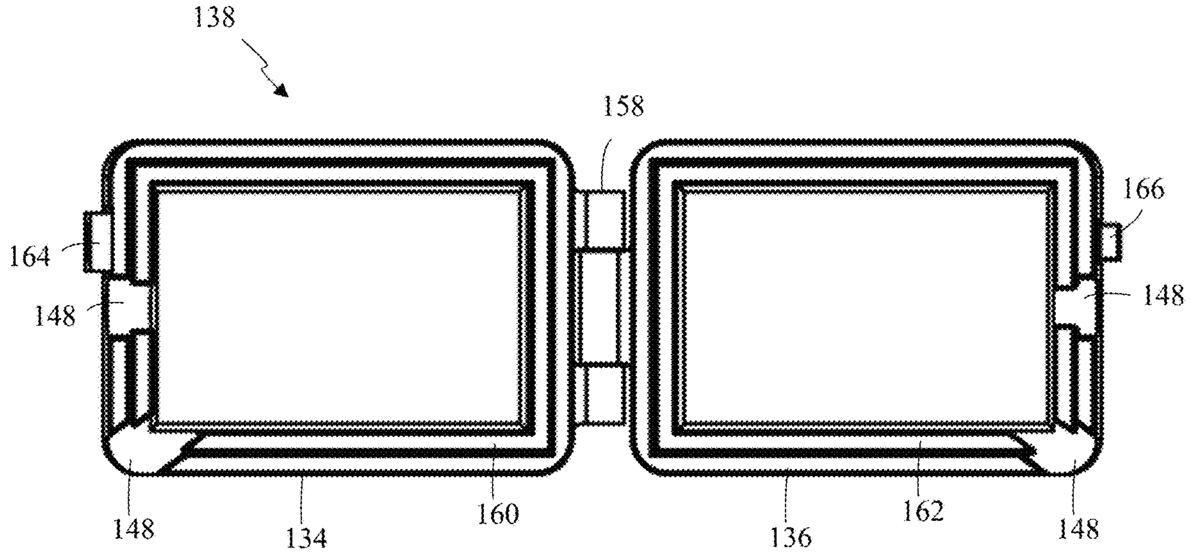
FIG. 29 is a plan view of an embodiment of a trial cap.
Figure 30:
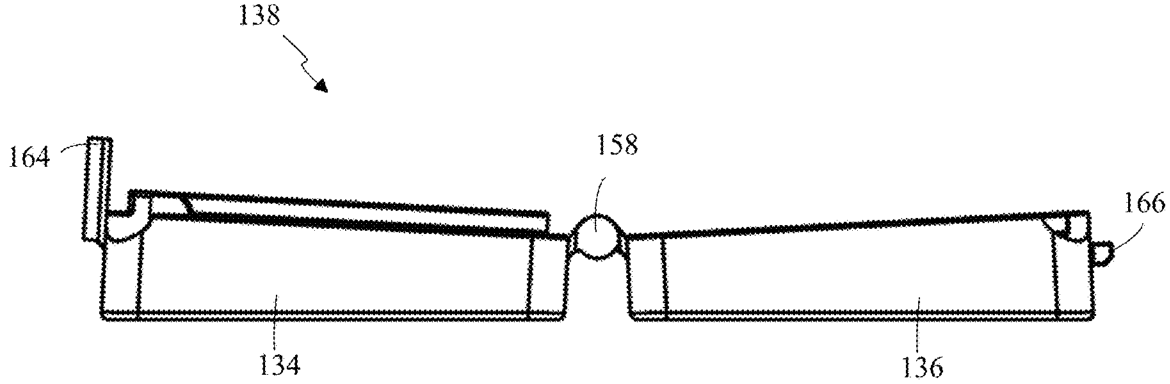
FIG. 30 is a side view of an embodiment of a trial cap.

As shown in FIGS. 28-30, some embodiments of trial caps 138 includes hinge mechanism 158 mechanically coupling first section 134 and second section 136. Hinge mechanism 158 allows the two sections to maintain a mechanical connection while also opening to receive trial base 116. Both sections 134 and 136 also include alignment structures, such as rectangular extension 160 and rectangular receipt 162. Rectangular extension 160 and rectangular receipt 162 have a corresponding size and shape sufficient to ensure that sections 134 and 136 are properly aligned when trial cap 138 is closed.

As also depicted in the same figures, some embodiments include interlocking components in the form of flexible or resilient tab 164 extending from first section 134 and protrusion 166 extending from second section 136. Tab 164 includes receipt 168 for receiving protrusion 166. When receipt 168 houses protrusion 166, trial cap 138 is considered to be in a locked orientation. A user can unlock trial cap 138 by flexing tab 164 until receipt 168 no longer houses protrusion 166 thereby allowing sections 134 and 136 to rotate about hinge mechanism 158 into an open position.

It is contemplated that other method and devices may be used to secure the two hingedly connected sections. Non-limiting examples include a bayonet lock, quick release pin mechanism, snap-fit connection, magnetic attachment, and press-fit connection.

Figure 31:
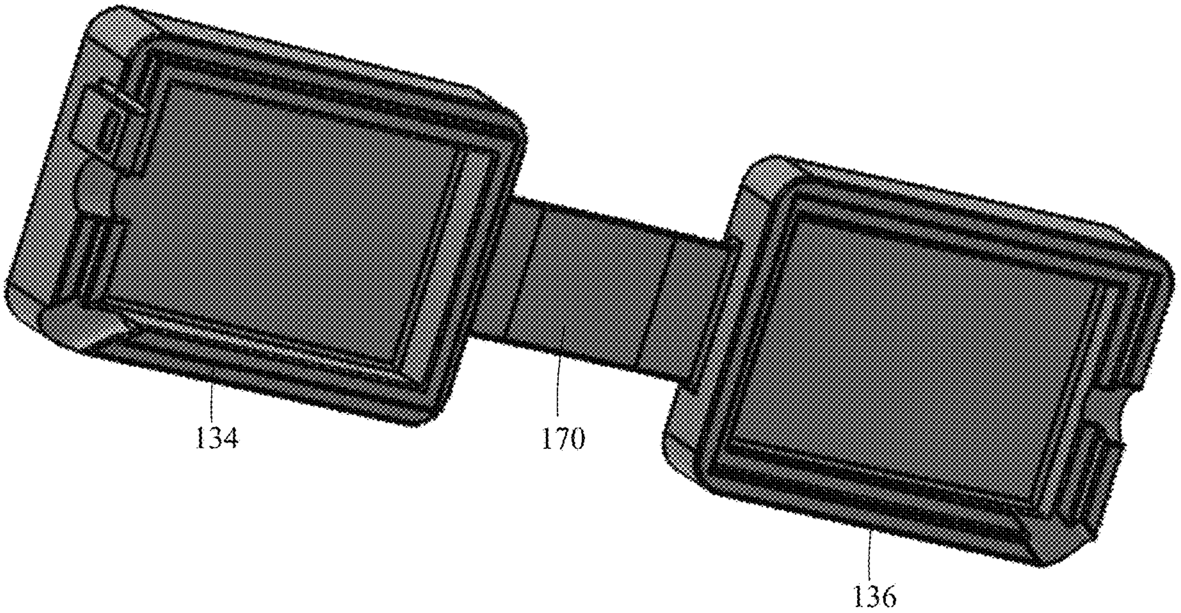
FIG. 31 is a perspective view of an embodiment of a trial cap.
Figure 32:
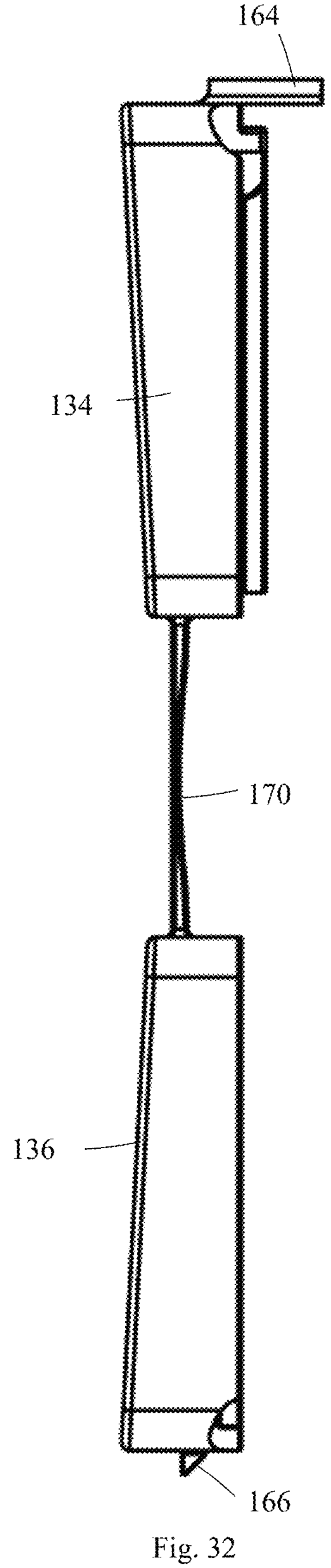
FIG. 32 is a side view of an embodiment of a trial cap.

As depicted in FIGS. 31-32, the hinge mechanism may be in the form of a "living hinge." Living hinge 170 may be a thin, flexible member of material that connects to sections 134 and 136. Living hinge 170 allows sections 134 and 136 to bend or pivot relative to each other while maintaining structural integrity.

Figure 33:
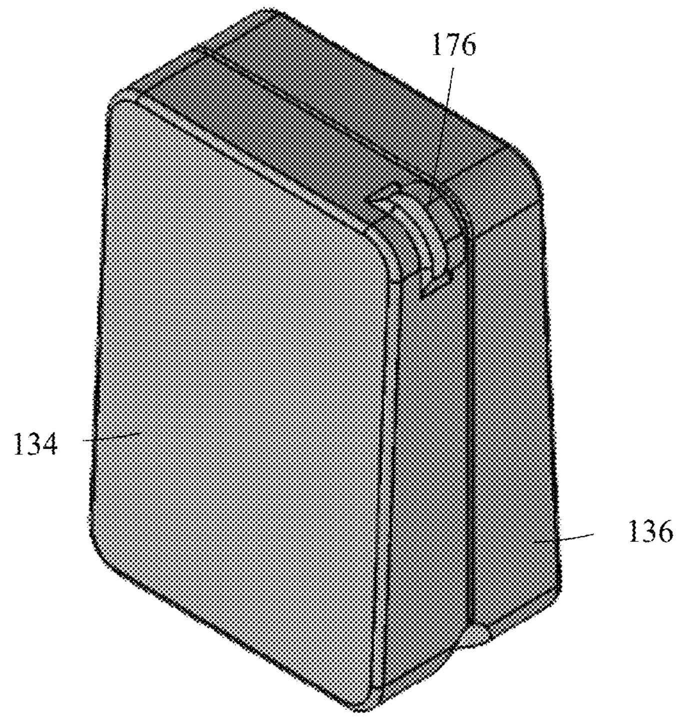
FIG. 33 is a perspective view of an embodiment of a trial cap.
Figure 34:
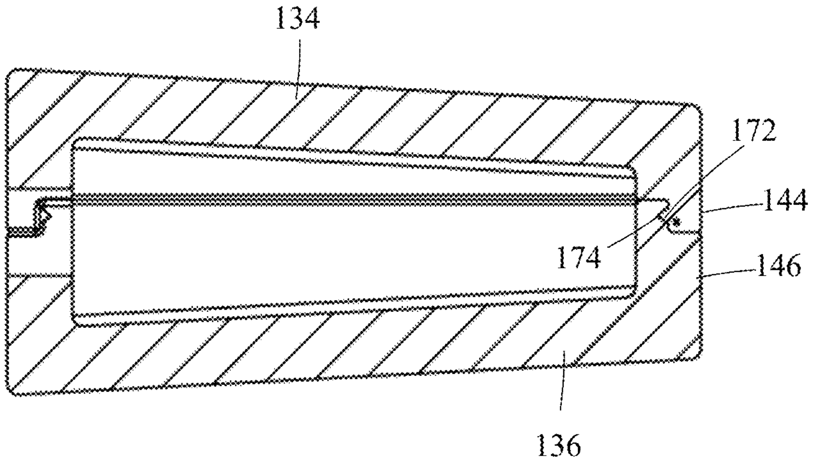
FIG. 34 is a cross-sectional view of an embodiment of a trial cap.
Figure 35:
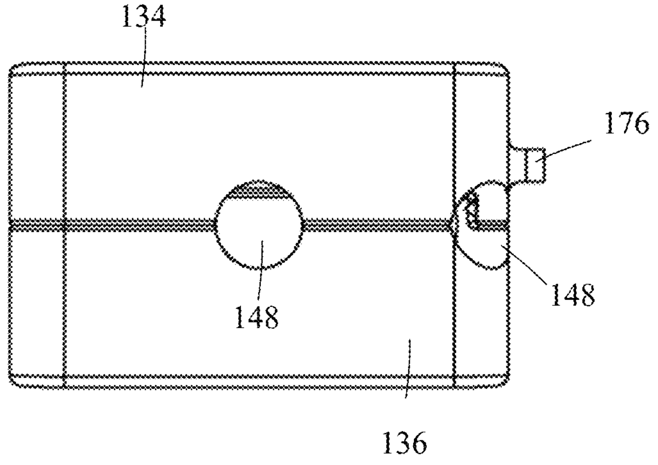
FIG. 35 is an end view of an embodiment of a trial cap.
Figure 36:
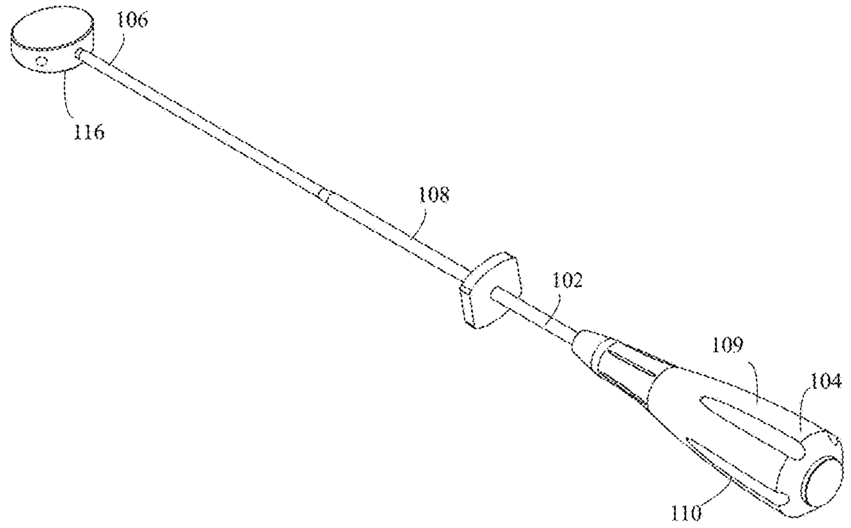
FIG. 36 is a perspective view of an embodiment of the trial inserter and the trial base attached thereto.
Figure 37:
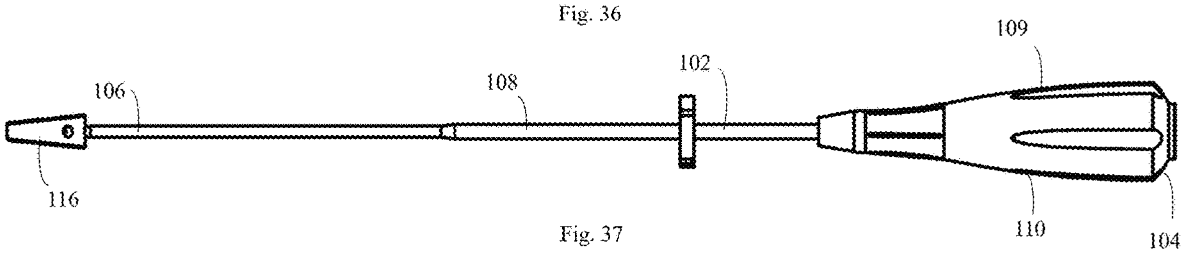
FIG. 37 is a side view of an embodiment of the trial inserter and the trial base attached thereto.
Figure 38:
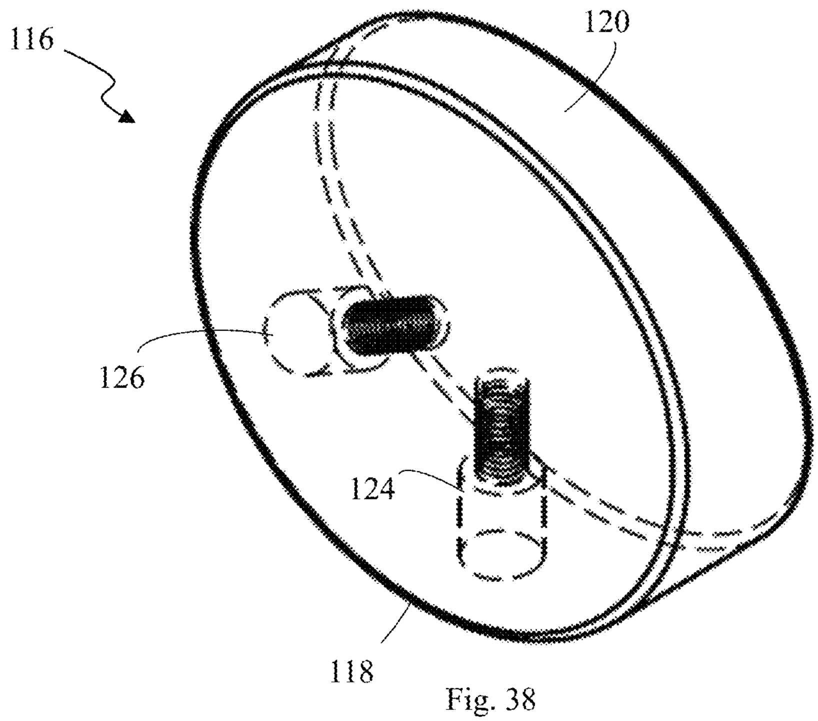
FIG. 38 is a perspective view of an embodiment of a trial base.

As another example, trial caps 138 may be completely detachable into independent sections 134 and 136 and employ interlocking components in the form of a snap-fit connection between the two sections 134 and 136 as depicted in FIGS. 33-35. The snap-fit connections may be in the form of catch 172 on one of sections 134 and 136 and slot/recess 174 on the other section. One or both of catch 172 and recess 174 may be flexible/resilient to enable the components to move into engagement as depicted in FIG. 34. The snap fitting typically relies on materials that have some elasticity, allowing the components to bend during the assembly process and then return to shape to lock in place. Nonlimiting exemplary material could be plastic, a flexible metal, or a composite material with sufficient durability. When sections 134 and 136 are pressed together the protrusions snap into the slots, securing the two halves without the need for additional fasteners.

In some embodiments, catch 172 and recess 174 are disposed in sidewalls 144 and 146 to minimize external interactions with the patient's tissue. Catch 172 and recess 174 may also extend about the entire perimeter be comprised of disjointed sections spaced about the perimeter to aid in the alignment of the two sections 134 and 136. In this manner, catch 172 and recess 174 also function as alignment structures.

As best depicted in FIG. 33, some embodiments of trial caps 138 further include one or more protruding handles 176 for easy separation of the two halves. Handle 176 may extend outwardly in a lateral direction in an amount sufficient to allow a user to apply a force to open trial caps 138, but also maintain a relatively low profile to limit the interaction with the patient's tissue.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. An adjustable trial spacer system, comprising:

a trial base having a predetermined thickness, wherein the trial base includes an attachment feature configured to engage a trial inserter;

a plurality of trial caps, each trial cap including:

a predetermined thickness that is greater than the predetermined thickness of the trial base and distinct from other trial caps;

a first section and a second section, the first section and the second section configured to temporarily connect to each other and house at least a portion of the trial base, and the first section and the second section further configured to detach from each other; and one or more interlocking components to securely attach the first section to the second section, wherein the one or more interlocking components include an extension projecting inwardly from the first section, and a receipt extending inwardly from the second section, the receipt configured to engage the extension when the first section and the second section are attached, and the trial base including a retention aperture configured to enable passage of the extension therethrough.

2. The system of claim 1, wherein the first section and the second section of each trial cap further include a recess configured to receive a portion of the trial base.

3. The system of claim 1, wherein each trial cap includes an aperture that aligns with the attachment feature in the trial base when the trial base resides within the trial cap.

4. The system of claim 1, wherein the attachment feature in the trial base is a threaded aperture configured to threadedly engage the trial inserter.

5. The system of claim 1, wherein the trial base has a tapered profile.

6. The system of claim 1, wherein each trial cap has a tapered profile.

7. An adjustable trial spacer system, comprising:

a trial inserter having an elongated shaft;

a trial base having a predetermined thickness, wherein the trial base includes an attachment feature configured to engage the trial inserter;

a plurality of trial caps, each trial cap including:

a first section and a second section, wherein the first section and the second section are configured to sandwich the trial base;

a predetermined thickness when sandwiching the trial base that is greater than the predetermined thickness of the trial base and distinct from other trial caps; and one or more interlocking components to securely attach the first section to the second section, wherein the one or more interlocking components include an extension projecting inwardly from the first section, and a receipt extending inwardly from the second section, the receipt configured to engage the extension when the first section and the second section are attached, and the trial base including a retention aperture configured to enable passage of the extension therethrough.

8. The system of claim 7, wherein the first section and the second section of each trial cap further include a recess configured to receive a portion of the trial base.

9. The system of claim 7, wherein each trial cap includes an aperture that aligns with the attachment feature in the trial base when the trial base resides within the trial cap.

10. The system of claim 7, wherein the shaft of the trial inserter has a threaded section and the attachment feature in the trial base is a threaded aperture configured to threadedly engage the threaded section of the trial inserter.

11. The system of claim 7, wherein the trial base has a tapered profile.

12. The system of claim 7, wherein each trial cap has a tapered profile.

13. An adjustable trial spacer system, comprising:

a trial base having a predetermined thickness, wherein the trial base includes an attachment feature configured to engage a trial inserter;

a plurality of trial caps, each trial cap including:

a predetermined thickness that is greater than the predetermined thickness of the trial base and distinct from other trial caps;

a first section and a second section, wherein the first section and the second section are configured to temporarily house at least a portion of the trial base; and one or more interlocking components to securely attach the first section to the second section and retain the trial base between the first section and the second section, wherein the one or more interlocking components include an extension projecting inwardly from the first section, and a receipt extending inwardly from the second section, the receipt configured to engage the extension when the first section and the second section are attached, and the trial base including a retention aperture configured to enable passage of the extension therethrough.

14. The system of claim 13, wherein the first section and the second section of each trial cap further include a recess configured to receive a portion of the trial base.

15. The system of claim 13, wherein each trial cap includes an aperture that aligns with the attachment feature in the trial base when the trial base resides within the trial cap.

16. The system of claim 13, wherein each trial cap has a tapered profile.

* * * * *